US008364238B2

(12) United States Patent
Fadem (10) Patent No.: US 8,364,238 B2
(45) Date of Patent: Jan. 29, 2013

(54) ELECTRODE SYSTEM

(75) Inventor: Kalford C. Fadem, Louisville, KY (US)

(73) Assignee: Neuronetrix Solutions, LLC, Louisville, KY (US)

(*) Notice: Subject to any disclaimer, the term of this patent is extended or adjusted under 35 U.S.C. 154(b) by 408 days.

(21) Appl. No.: 12/617,786

(22) Filed: Nov. 13, 2009

(65) Prior Publication Data
US 2010/0125190 A1 May 20, 2010

Related U.S. Application Data

(60) Provisional application No. 61/114,715, filed on Nov. 14, 2008.

(51) Int. Cl.
*A61B 5/0478* (2006.01)
(52) U.S. Cl. ........................... 600/383; 600/393
(58) Field of Classification Search .......... 600/383, 600/393
See application file for complete search history.

(56) References Cited

U.S. PATENT DOCUMENTS

| | | | | |
|---|---|---|---|---|
| 5,038,782 | A * | 8/1991 | Gevins et al. | 600/383 |
| 5,479,934 | A * | 1/1996 | Imran | 600/544 |
| 2005/0215916 | A1 | 9/2005 | Fadem et al. | |
| 2005/0251003 | A1 | 11/2005 | Istvan et al. | |
| 2007/0106169 | A1 | 5/2007 | Fadem | |
| 2007/0191727 | A1 | 8/2007 | Fadem | |
| 2007/0225585 | A1* | 9/2007 | Washbon et al. | 600/393 |
| 2007/0270678 | A1 | 11/2007 | Fadem et al. | |
| 2008/0114220 | A1 | 5/2008 | Banet et al. | |
| 2008/0208072 | A1 | 8/2008 | Fadem et al. | |

OTHER PUBLICATIONS

U.S. Appl. No. 61/245,686, filed Sep. 25, 2009, Fadem.
International Search Report and Written Opinion dated Jan. 20, 2010 for Application No. PCT/US2009/064320.

* cited by examiner

*Primary Examiner* — Lee S Cohen
(74) *Attorney, Agent, or Firm* — Frost Brown Todd LLC (57) ABSTRACT

An electrode system comprises electrode modules, flexible connectors, and sensors. Each electrode module defines a substantially central opening and has circuitry that includes an amplifier. A conductive ring is exposed in the opening of each electrode module. The flexible connectors include flexible circuitry coupled with the circuitry of the electrode modules. Each sensor includes an electrolytic hydrogel portion that is configured to contact a test subject and outwardly extending tabs that are in communication with the hydrogel portion. The tabs are configured to contact the conductive ring of an electrode module with the sensor is inserted in the opening of the electrode module. The system may thus sense evoked response potentials (ERPs) from the test subject through the electrolytic hydrogel portions, amplify those potentials, and communicate the amplified potentials through the circuitry of the flexible connectors. A control box may initiate ERP testing and store the test results.

16 Claims, 7 Drawing Sheets

ELECTRODE SYSTEM

PRIORITY

This application claims priority to U.S. Provisional Patent Application Ser. No. 61/114,715, filed Nov. 14, 2008, entitled "Electrode System," the disclosure of which is incorporated by reference herein.

BACKGROUND

In some settings, it may be desirable to position a headset with electrodes on a test subject's head, such as to test the subject for various conditions, including but not limited to various types of diseases or conditions within the cerebral cortex, Alzheimer's, Parkinson's, dyslexia, autism, and/or schizophrenia, among other conditions. For instance, one or more system components may be used to provide one or more types of stimuli to the test subject (e.g., auditory, visual, and/or tactile stimulus, etc.); and electrodes may be used to detect Evoked Response Potentials (ERP's) associated with such stimuli. By way of example only, active or locally amplified electrodes, as well as related systems and methods, are discussed in the following documents, each of which is incorporated by reference herein: U.S. Pat. No. 5,479,934, entitled "EEG Headpiece with Disposable Electrodes and Apparatus and System and Method for Use Therewith," issued Jan. 2, 1996; U.S. Pub. No. 2005/0215916, entitled "Active, Multiplexed Digital Electrodes for EEG, ECG, and EMG Applications," published Sep. 29, 2005; U.S. Pub. No. 2007/0106169, entitled "Method and System for an Automated E.E.G. System for Auditory Evoked Responses," published May 10, 2007; U.S. Pub. No. 2007/0270678, entitled "Wireless Electrode for Biopotential Measurement," published Nov. 22, 2007; and U.S. Pub. No. 2007/0191727, entitled "Evoked Response Testing System for Neurological Disorders," published Aug. 16, 2007. Copies of those documents are also appended hereto.

It should be understood that the teachings herein may be applied to or otherwise combined with any of the systems and methods taught in all of the above-cited documents.

While a variety of electrode systems have been made and used, and while a variety of methods have been used to construct such electrode systems, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Exemplary System Overview

Figure 1:
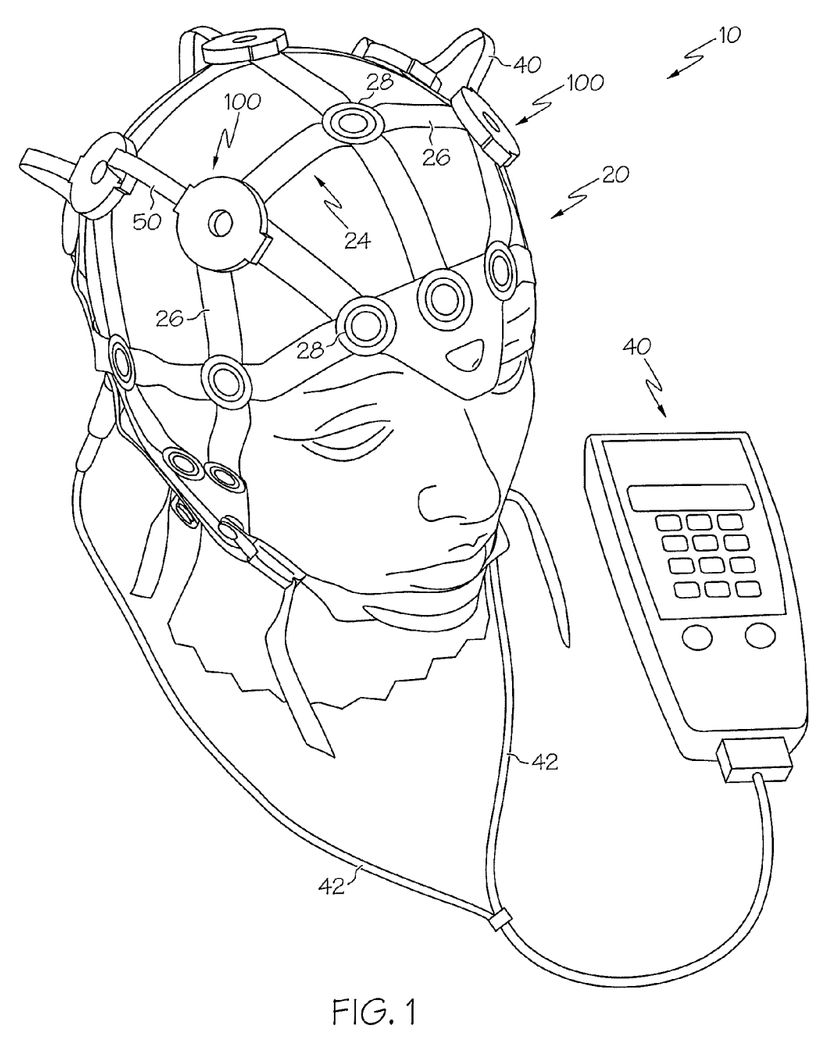
FIG. 1 depicts a perspective view of an exemplary ERP testing system.
Figure 2:
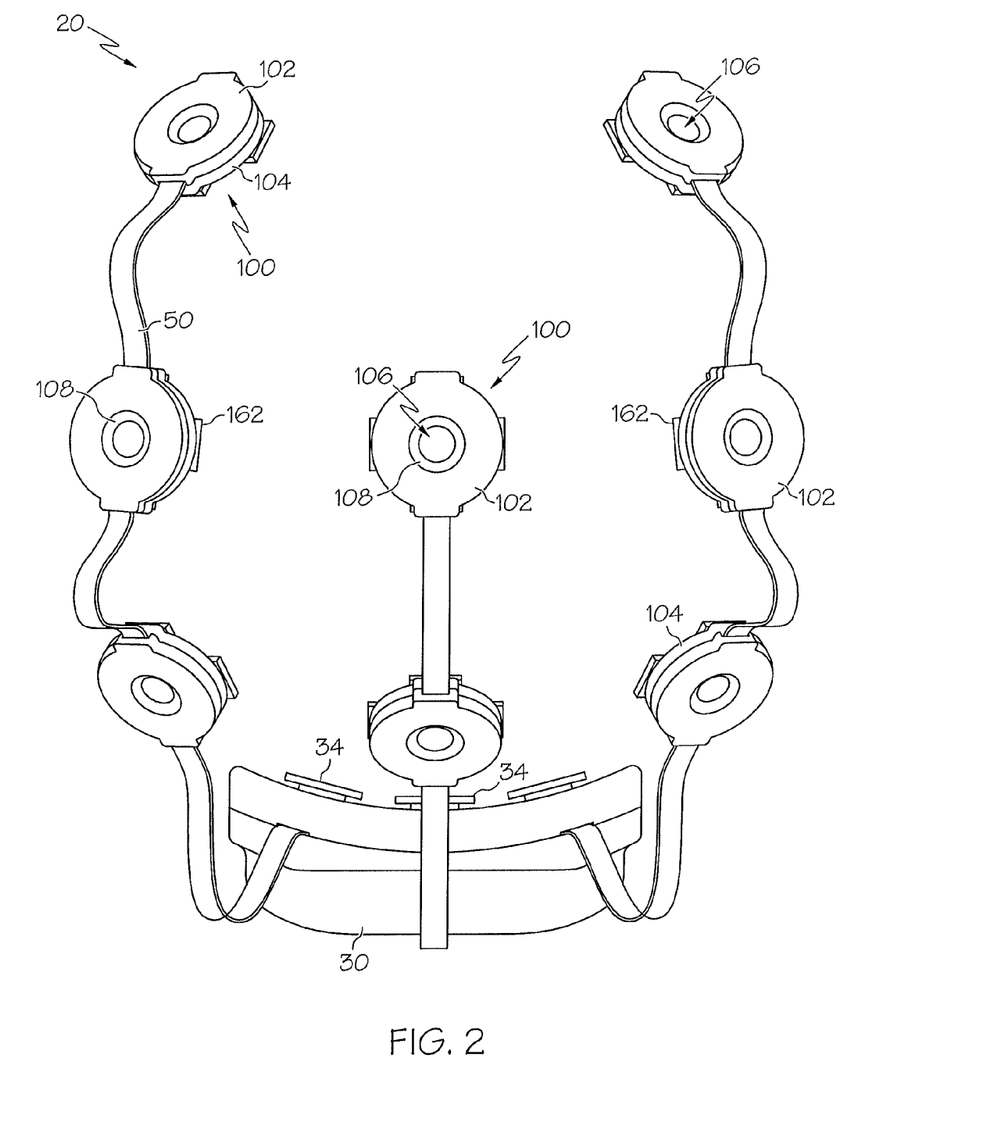
FIG. 2 depicts a top plan view of electrode components of the ERP testing system of FIG. 1.
Figure 3:
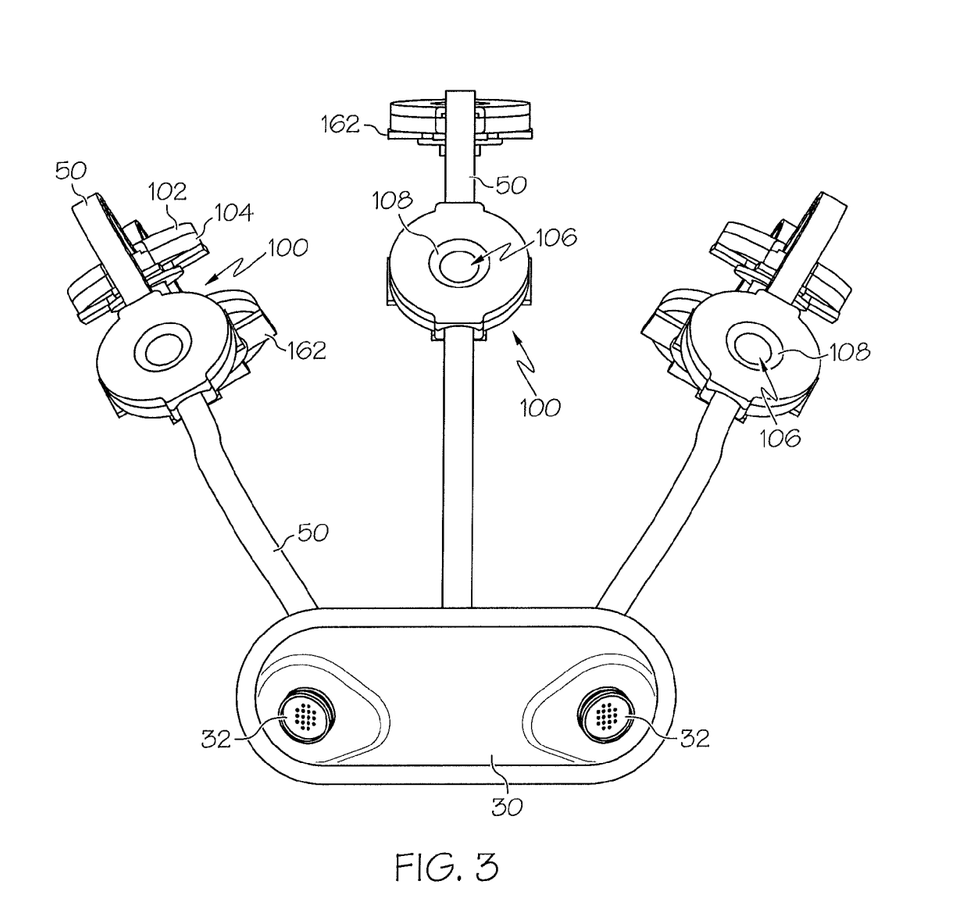
FIG. 3 depicts a rear elevational view of the electrode components of FIG. 2.
Figure 4:
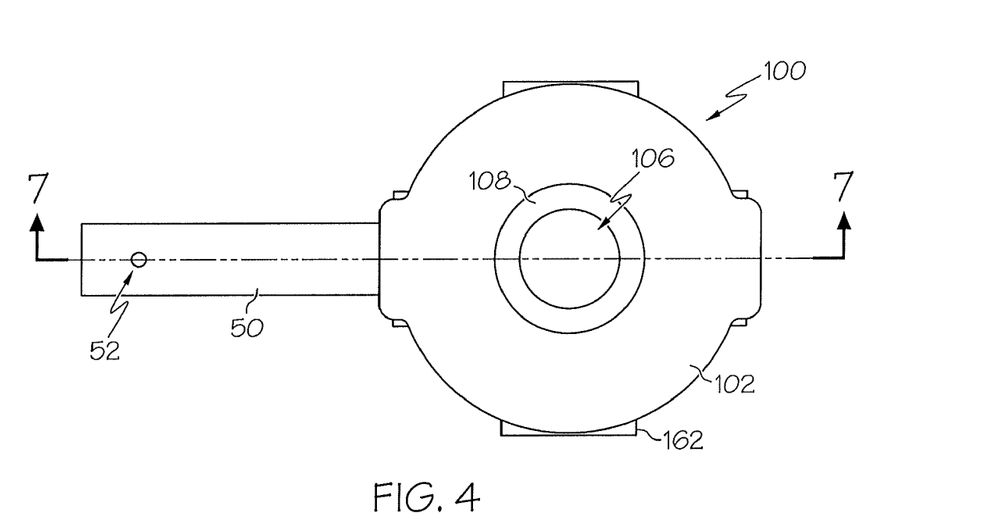
FIG. 4 depicts a top plan view of an electrode module of the electrode components of FIG. 2.

As shown in FIG. 1, an exemplary electrode system (10) includes a headset (20) and a control box (40). Headset (20) comprises a head frame (24) and a plurality of electrode modules (100). While headset (20) of the present example comprises eight electrode modules (100), it should be understood that any other suitable number of electrode modules (100) may be used. It should also be understood that the arrangement of electrode modules (100) shown in FIGS. 1-3 is merely exemplary; and that electrode modules (100) may be positioned in any other suitable arrangement. Electrode modules (100) are removably coupled with head frame (24) as will be described in greater detail below.

Exemplary Head Frame

In the present example, head frame (24) is formed of several resilient straps (26), and electrode modules (100) are secured to head frame (24) at junctions of resilient straps (26). The junctions of resilient straps (26) comprise annular snap members (28), which are each open at their center. As will be described in greater detail below, openings (106) of electrode modules (100) are configured to align with the open centers of corresponding snap members (28), to allow inserted sensors (200) to contact the test subject's head. In some versions, resilient straps (26) are formed of elastic, though it should be understood that any other suitable material or combination of materials may be used. While head frame (24) of the present example is configured to substantially encompass a test subject's head, it should also be understood that head frame (24) may have any other suitable configuration. By way of example only, head frame (24) may comprise a EzeNet® reusable head piece by HydroDot, Inc. of Westford, Mass. A EzeNet® reusable head piece may come in various sizes and conform to the international 10/20 system of electrode placement.

As another merely illustrative example, head frame (24) may be configured and/or operable in accordance with the teachings of U.S. Pub. No. 2007/0191727, entitled "Evoked Response Testing System for Neurological Disorders," published Aug. 16, 2007, the disclosure of which is incorporated by reference herein; and/or in accordance with the teachings of any other document cited herein. Indeed, various ways in which the teachings herein may be combined with the teachings of U.S. Pub. No. 2007/0191727 and/or the teachings of any other document cited herein will be apparent to those of ordinary skill in the art. Alternatively, head frame (24) may have any other suitable configuration and/or operability. Other suitable variations of head frame (24) will be apparent to those of ordinary skill in the art in view of the teachings herein.

As shown in FIGS. 1-3, electrode modules (100) are physically and communicatively coupled with each other via flexible connectors (50). Electrode modules (100) are also physically and communicatively coupled with a control box interface module (30) via flexible connectors (50). Flexible connectors (50) of the present example comprise flexible circuits, which comprise traces (not shown) formed in a flexible substrate. Alternatively, conventional wires or other conduits may be used. In the present example, headset (20) is coupled with control box (40) via cables (42). In particular, control box interface module (30) includes ports (32), with which cables (42) may be coupled. Control box interface module (30) also includes circuitry configured to route signals between flexible connectors (50) and cables (42) via ports (32). Control box interface module (30) may thus provide a communicative interface between cables (42) and flexible connectors (50). Various suitable components that may be incorporated into control box interface module (30), as well as various suitable features/functionalities of such components, are described in the documents cited herein. By way of example only, control box interface module (30) may be constructed and operable in accordance with the headset "control module 12" teachings of U.S. Pub. No. 2007/0191727 and/or the teachings of any other document cited herein. Still other suitable components that may be incorporated into control box interface module (30) will be apparent to those of ordinary skill in the art in view of the teachings herein.

In the present example, and as shown in FIG. 2, control box interface module (30) also includes flanged members (34). Flange members (34) are configured to secure control box interface module (30) with head frame (24). For instance, head frame (24) may include openings that are configured to receive flanged members (34). Of course, control box interface module (30) may be secured to head frame (24) in a variety of other ways as will be appreciated by those of ordinary skill in the art, to the extent that control box interface module (30) is secured to head frame (24) at all. Furthermore, control box interface module (30) may simply be omitted in some versions (e.g., cables (42) couple directly to freely hanging flexible connectors (50), etc.).

Exemplary Control Box

Control box (40) of the present example includes a storage medium (not shown) that is configured to store various testing protocols (e.g., ERP testing protocols, etc.); and a processor (not shown) that is configured to execute such testing via headset (20). In particular, control box (40) provides power and commands or other types of signals to headset (20) via cables (42) in the present example; while headset (20) transmits data or other types of signals back to control box (40) via cables (42). Control box (40) is also operable to store data collected during such testing, including but not limited to data obtained through electrode modules (100). Such power, commands, data, or other types of signals may be provided in accordance with various types of ERP testing protocols as described herein and as described in the documents that are incorporated by reference herein.

Control box (40) is configured to be coupled with a computer system (not shown) via wire and/or wirelessly. For instance, a computer system may transmit testing protocols, commands, or other data to control box (40). Similarly, control box (40) may transmit commands, test results, or other data to a computer system. Control box (40) of the present example is also configured to be handheld. By way of example only, control box (40) may be held in the hand of the test subject who is wearing headset (40), in the hand of a clinician or nurse, or in the hand of any other person. In addition to or in lieu of the foregoing, control box (40) may be configured in accordance with, operable in accordance with, and/or possess any suitable features/functionalities of similar components described in any of the documents cited herein, including but not limited to U.S. Pub. No. 2007/0191727.

Various ways in which the teachings herein may be incorporated into or otherwise combined with the teachings of the documents that are cited herein will be readily apparent to those of ordinary skill in the art.

While two cables (42) are shown, it should be understood that just one cable (42) may be used. It should also be understood that some other versions of electrode system (10) may provide communication of power, commands, data, and/or other types of signals to and/or from headset (20) wirelessly, in addition to or in lieu of having cables (22).

Exemplary Electrode Module

In the present example, electrode modules (100) of electrode system (10) are substantially identical to each other. The following description will therefore just describe an individual electrode module (100) as an example. It should be understood, however, that a given electrode system (10) may have different types of electrode modules (100). In other words, one or more electrode modules (100) within a given electrode system (10) may have features, components, functionalities, etc., that differ from the features, components, functionalities, etc., of other electrode modules (100) within the same electrode system (10). Such differences among electrode modules (100) may be based on a variety of considerations, including but not limited to the location of electrode module (100) on the test subject's head or other part of the test subject's anatomy. Suitable ways in which electrode modules (100) may differ from each other within a given electrode system (10) will be apparent to those of ordinary skill in the art in view of the teachings herein. Alternatively, as in the present example, all electrode modules (100) within a given electrode system (10) may be substantially identical to each other.

As shown in FIGS. 2-7, electrode module (100) comprises an upper clamshell member (102), a lower clamshell member (104), a circuit board (130), and a conductive ring (150). Clamshell members (102, 104) may be formed of molded plastic and/or using any other suitable material(s) and/or process(es). As shown, upper clamshell member (102), lower clamshell member (104), circuit board (130), and conductive ring (150) all define a central opening (106). In particular, the central openings of upper clamshell member (102), lower clamshell member (104), circuit board (130), and conductive ring (150) are all configured to coaxially align when these components are assembled together to form electrode module (100), such that the assembled electrode module (100) itself defines a central opening (106). This central opening (106) is configured to insertingly receive a sensor (200) as will be described in greater detail below. In addition, these components are configured such that a portion of conductive ring (150) is exposed in the inner diameter of the central opening (106) of the assembled electrode module (100), as will also be described in greater detail below. During assembly of electrode module (100), upper clamshell member (102) may be secured to lower clamshell member (104) using any suitable technique or techniques, including but not limited to ultrasonic welding, snap-fitting, adhesives, fasteners, etc. While opening (106) is at the approximate center of electrode module (100) in the present example, it should be understood that opening (106) may be located off-center or otherwise relative to the remainder of electrode module (100).

Upper clamshell member (102) of the present example presents an annular inclined surface (108) at the perimeter of opening (106). Annular inclined surface (108) is configured to facilitate insertion of sensor (200) into opening (106) as will be described in greater detail below. Of course, as with other components and features described herein, inclined surface (108) is merely optional. Lower clamshell member (104) of the present example comprises a first pair of upwardly extending posts (110) and a second pair of upwardly extending posts (112). Lower clamshell member (104) also includes an annular rim (114) at the perimeter of opening (106) and a trench (116) adjacent to annular rim (114).

Each of these features of lower clamshell member (104) will be described in greater detail below.

Figure 5:
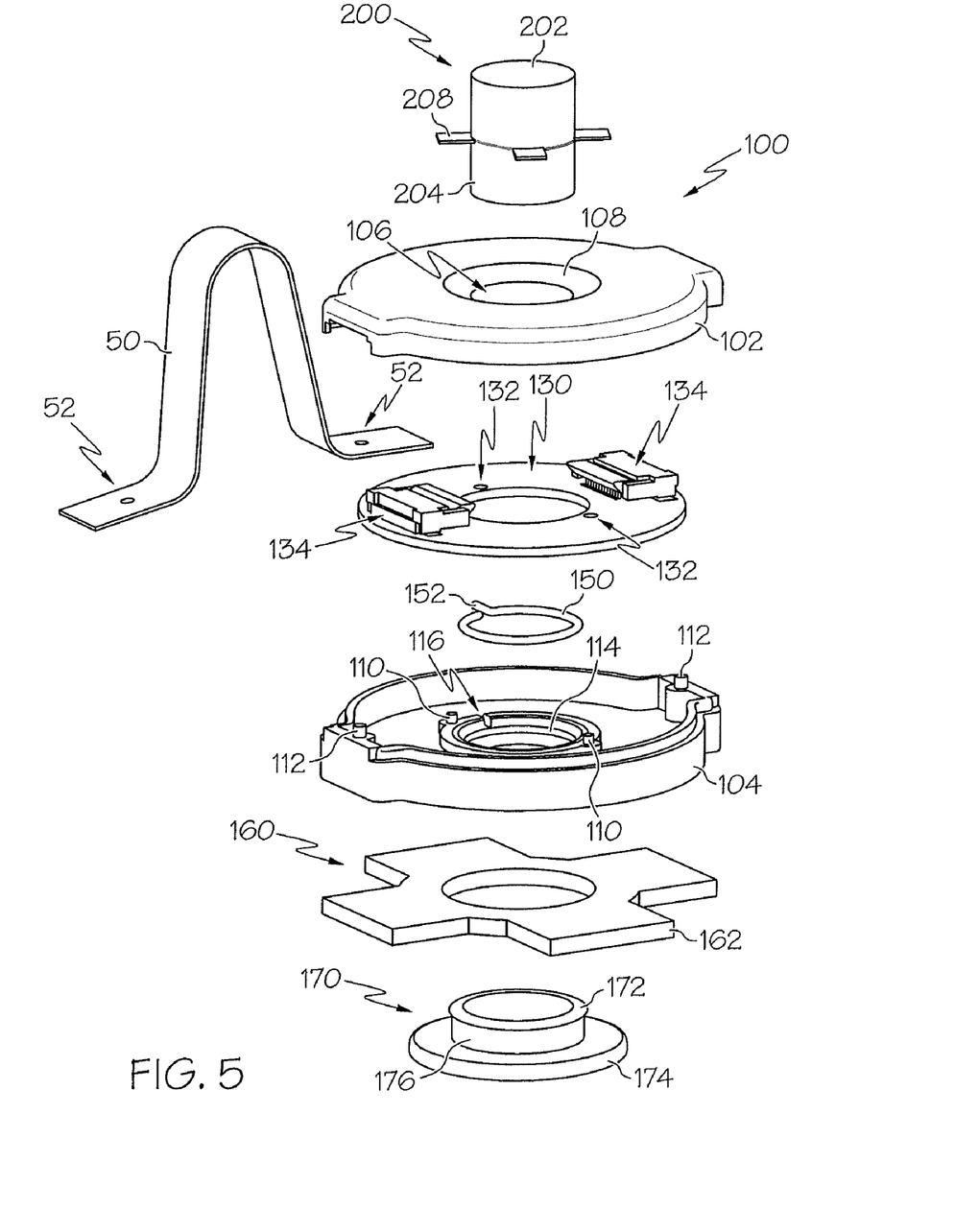
FIG. 5 depicts an exploded perspective view of the electrode module of FIG. 4, with an exemplary sensor.
Figure 6:
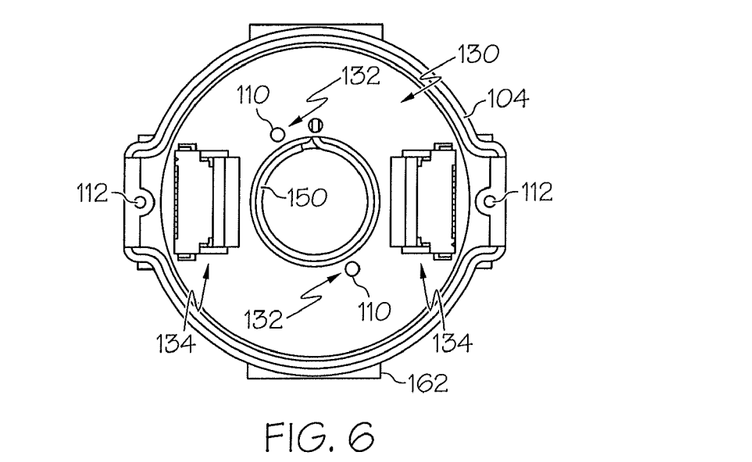
FIG. 6 depicts a top plan view of the electrode module of FIG. 4, with a top housing component and flex circuit component removed.

Circuit board (130) of the present example comprises a pair of openings (132) and a pair of connectors (134). As shown in FIGS. 5-6, openings (132) of circuit board (130) are configured to align with and receive posts (110) of lower clamshell member (104). Openings (132) and posts (110) may thus assist in properly registering circuit board (130) with lower clamshell member (104) and assist in securing circuit board (130) relative to lower clamshell member (104). Of course, openings (132) and posts (110) are merely one of many different ways in which circuit board (130) may be registered and secured relative to lower clamshell member (104). Various other structures, features, techniques, etc. for registering and/or securing circuit board (130) relative to lower clamshell member (104) will be apparent to those of ordinary skill in the art in view of the teachings herein.

Figure 7:
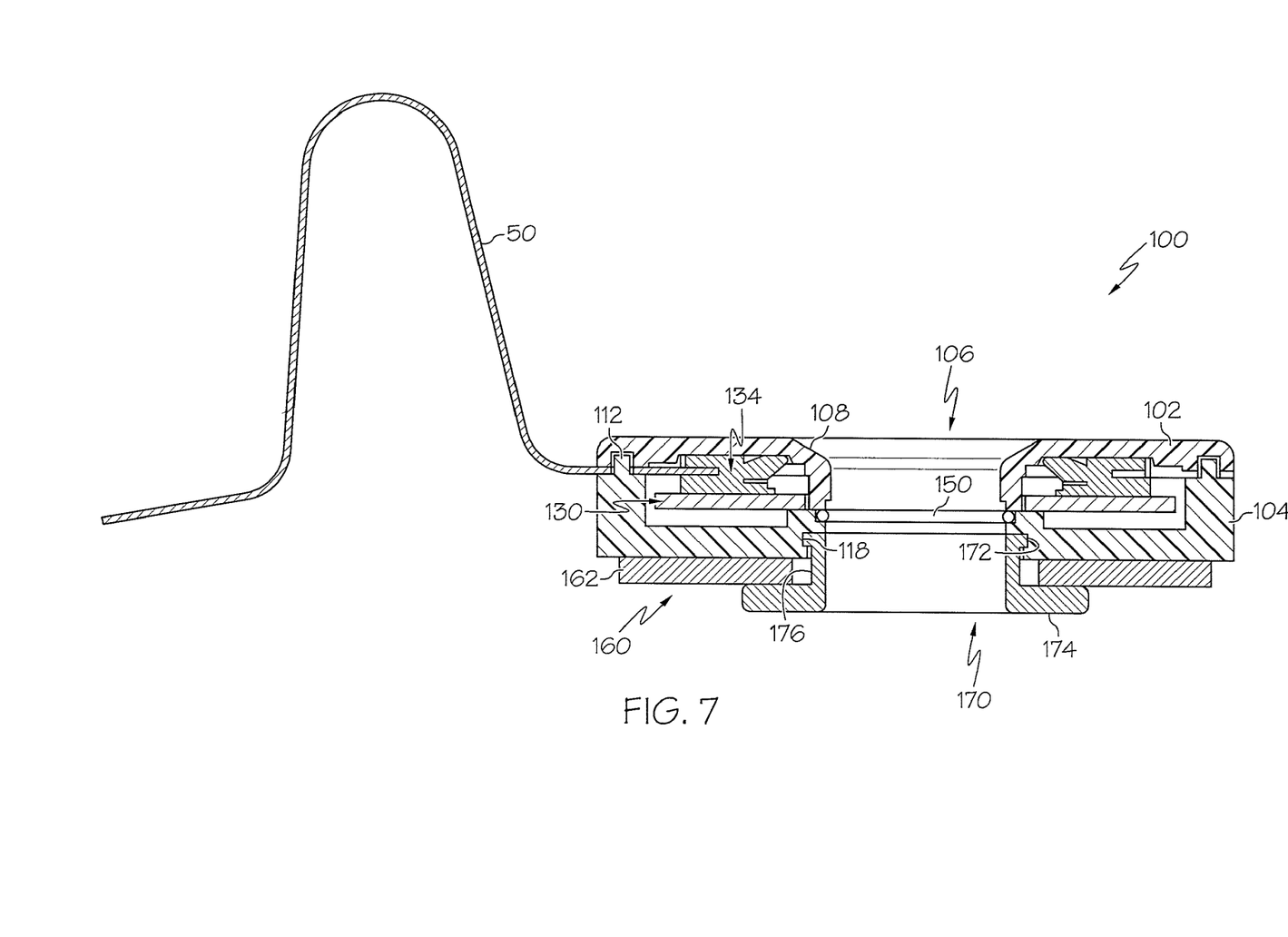
FIG. 7 depicts a cross-sectional side view of the electrode module of FIG. 4, taken along line 7-7 of FIG. 4.

Connectors (134) of circuit board (130) are configured to be physically and communicatively coupled with flexible connectors (50). In particular, each connector (134) has a slot that is configured to receive a free end of a corresponding flexible connector (50). Flexible connector (50) has an opening (52) that is configured to receive a post (112) of lower clamshell member (104). Thus, when flexible connector (50) is inserted in the slot of connector (134), with post (112) inserted through opening (52) of flexible connector (50), and when clamshell members (102, 104) are secured relative to each other as shown in FIG. 7, the insertion of post (112) through opening (52) may substantially prevent flexible connector (50) from being pulled out of connector (134). In addition, connector (134) may have one or more exposed/exposable electrical contacts within its slot; while the free end of flexible connector (50) may have one or more corresponding electrical contacts that are positioned to contact the one or more exposed/exposable electrical contacts within the slot of connector (134).

Connector (134) may thus communicate power, commands, data, other signals, etc., to and/or from one or more traces of flexible connector (50).

Of course, connectors (134) are merely optional, and connectors (134) may be modified, substituted, supplemented, or omitted as desired. By way of example only, some alternative versions omit connectors (134) entirely by forming all flexible connectors (50) and circuit boards (130) as a single, unitary rigid-flex circuit. A merely illustrative example of such a rigid-flex circuit is disclosed in U.S. Provisional Patent Application Ser. No. 61/245,686, entitled "Electrode System with Rigid-Flex Circuit," filed Sep. 25, 2009, the disclosure of which is incorporated by reference herein. Still other suitable ways in which connectors (134) may be modified, substituted, supplemented, or omitted will be apparent to those of ordinary skill in the art in view of the teachings herein.

As shown in FIGS. 1-3 and as noted above, electrode modules (100) are coupled via flexible connectors (50). In some versions, different electrode modules (100) have their own dedicated traces along such flexible connectors (50). Dedicated traces for a given electrode module (100) may run along part of the same length of flexible connectors (50) as dedicated traces for another given electrode module (100). For instance, a set of dedicated traces for one electrode module (100) may be provided on one layer of flexible circuitry in a given flexible connector (50); while a set of dedicated traces for another electrode module (100) may be provided on another layer of flexible circuitry on the same flexible connector (50), with both layers extending along a common length of the flexible circuitry of the same flexible connector (50). As another merely illustrative example, dedicated traces for one electrode module (100) may be provided on the same layer of flexible circuitry as dedicated traces for another electrode module (100), such that the separate sets of traces are geometrically parallel on a common layer. In some other versions, different electrode modules (100) may share one or more common traces in a given flexible connector (50). By way of example only, one or more traces in flexible circuitry of flexible connectors (50) may be used for bus transmissions, such that information associated with different electrode modules (100) may be combined onto a bus and communicated along one or more non-dedicated traces that are in communication with more than one electrode module (100). Various other suitable ways in which traces or other communication features may be used, provided, arranged, etc., will be apparent to those of ordinary skill in the art in view of the teachings herein.

Circuit board (130) in each electrode module (100) of the present example also comprises sensing circuitry (not shown), which includes an amplifier among other components. Such sensing circuitry is in communication with connectors (134) of circuit board (130), such that the sensing circuitry may communicate with the one or more traces of flexible connectors (50). With the sensing circuitry of circuit board (130) including an amplifier in the present example, it should be understood that electrode modules (100) are thus active. Such sensing circuitry may be configured and/or operable in accordance with the teachings of U.S. Pub. No. 2005/0215916, entitled "Active, Multiplexed Digital Electrodes for EEG, ECG, and EMG Applications," published Sep. 29, 2005, the disclosure of which is incorporated by reference herein; and/or in accordance with the teachings of any other document cited herein. Indeed, various ways in which the teachings herein may be combined with the teachings of U.S. Pub. No. 2005/0215916 and/or the teachings of any other document cited herein will be apparent to those of ordinary skill in the art. Alternatively, the sensing circuitry of circuit board (130) may have any other suitable configuration and/or operability. For instance, some versions of circuit board (130) may lack an amplifier, such that electrode modules (100) are not active. Still other suitable ways in which circuit board (130) may be configured, including but not limited to various forms and components of sensing circuitry, will be apparent to those of ordinary skill in the art in view of the teachings herein.

In the present example, conductive ring (150) comprises a tail portion (152) that extends radially outwardly. Conductive ring (150) is configured to rest on annular rim (114) of lower clamshell member (104), with tail portion (152) projecting through trench (116) of lower clamshell member (104). Accordingly, annular rim (114), trench (116), and tail portion (152) cooperate to assist in properly registering conductive ring (150) with lower clamshell member (104) and assist in securing conductive ring (150) relative to lower clamshell member (104). Of course, these features are just an example, and various other structures, features, techniques, etc. for registering and/or securing conductive ring (150) relative to lower clamshell member (104) will be apparent to those of ordinary skill in the art in view of the teachings herein. As best seen in FIG. 7, upper clamshell member (102) is positionable over conductive ring (150) to further secure conductive ring (150) in place by "sandwiching" conductive ring (150) between clamshell members (102, 104). As noted above, a portion of conductive ring (150) is still exposed in the inner diameter of the central opening (106) of the assembled electrode module (100) (e.g., when upper clamshell member (102) is secured to lower clamshell member (104), etc.). Conductive ring (150) is also communicatively coupled with the sensing circuitry of circuit board (130) (e.g., through contact via tail portion (152), etc.). In particular, conductive ring (150) is configured to communicate ERP signals to the sensing circuitry of circuit board (130) as will be described in greater detail below.

Electrode modules (100) may be coupled with head frame (24) in a variety of ways. In the present example, electrode modules (100) are coupled with head frame (24) through snap fittings at snap members (28) of head frame (24). For instance, as shown in FIGS. 5-7, each electrode module (100) of the present example is provided with a snap adapter (170). Each snap adapter (170) comprises an upper flange (172), a lower flange (174), and a cylindraceous portion (176) extending vertically between upper and lower flanges (172, 174). Lower clamshell member (104) includes an annular recess (118) that is configured to snappingly receive upper flange (172) of snap adapter (170) as shown in FIG. 7. Snap adapter (170) thus couples with electrode module (100) through a snap fitting in the present example, though it should be understood that any other suitable features, components, techniques, etc., may be used to secure a snap adapter (170) with an electrode module (100). Alternatively, electrode module (100) may have an integral or unitary snap adapter, or may couple with head frame (24) in some other way.

In the present example, a pad (160) is secured to each snap adapter (170). Each pad (160) has a plurality of outwardly extending tabs (162) and is relatively soft. For instance, the configuration of pad (160) may reduce discomfort to a test subject when a clinician manipulates electrode modules (100) while electrode modules (100) are on the test subject's head. Pad (160) is configured to fit about cylindraceous portion (176) of snap adapter (170). As shown in FIG. 7, pad (160) is "sandwiched" between the lower surface of lower clamshell member (104) and the upper surface of lower flange (174). Of course, pad (160) may be coupled with electrode module (100) in a variety of other ways. By way of example only, pad (160) may be secured to electrode module by one or more clips, hook and loop fasteners, adhesives, etc. Alternatively, pad (160) may be omitted entirely. For instance, snap member (28) of head frame (24) may be positioned about cylindraceous portion (176) of snap adapter (170). Snap member (28) may thus be "sandwiched" between the lower surface of lower clamshell member (104) and the upper surface of lower flange (174), similar to pad (160) in FIG. 7. In the present example, however, snap adapter (170) snappingly engages with snap member (28) (e.g., such that at least a portion of snap member (28) is positioned below lower flange (174)).

As yet another merely illustrative variation, snap adapter (170) may simply be omitted. By way of example only, snap member (28) may itself snappingly engage with lower clamshell member (104). For instance, snap member (28) may include an outwardly extending annular flange that is snappingly received in annular recess (188) of lower clamshell member (104). As still another merely illustrative variation, electrode modules (100) may couple directly with head frame (24), such that no snap fittings are used to couple electrode modules (100) with head frame (24). By way of example only, electrode modules (100) may be coupled with head frame (24) by one or more clips, hook and loop fasteners, adhesives, etc. In addition, while electrode modules (100) are removably coupled with head frame (24) in the present example, electrode modules (100) may be permanently affixed to head frame (24) in some other versions.

It should also be understood that when several snap member (28) (or other types of electrode module (100) engagement structures) and resilient straps (26) are arranged to provide a head frame (24), some snap members (28) may not have a corresponding electrode module (100) coupled thereto. It should therefore be understood that some headsets (20) may be configured to accommodate different kinds of electrode systems that have different numbers of and/or arrangements of electrode modules (100), providing a degree of modularity. Still other suitable ways in which electrode modules (100) may be incorporated into a headset (20) will be apparent to those of ordinary skill in the art in view of the teachings herein.

Exemplary Sensors

Figure 8:
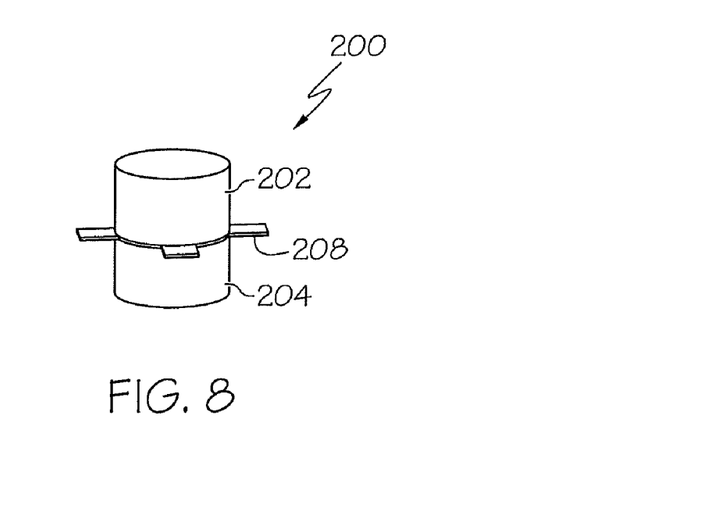
FIG. 8 depicts a perspective view of an exemplary sensor for use with the ERP testing system of FIG. 1.
Figure 9:
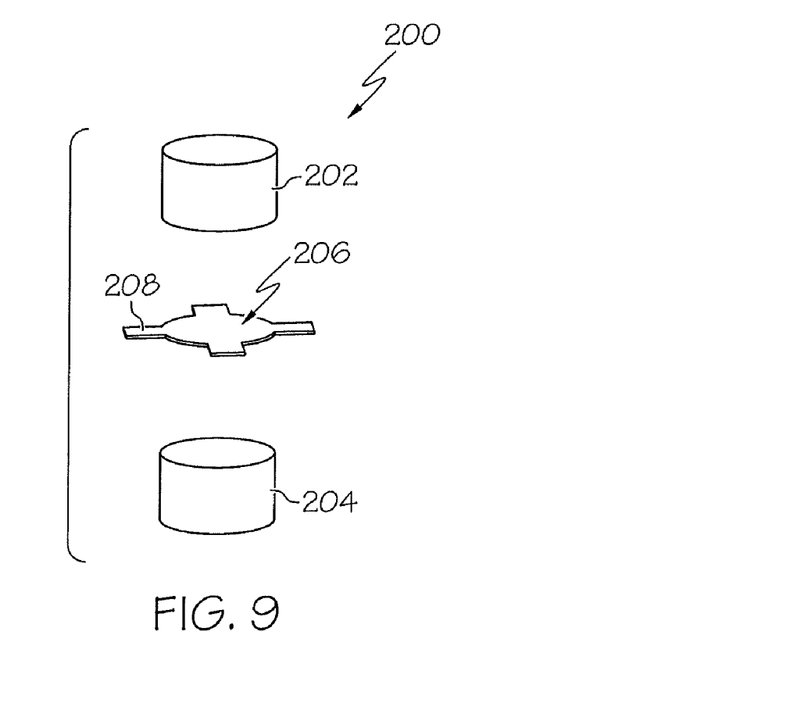
FIG. 9 depicts an exploded view of the sensor of FIG. 8.

As shown in FIGS. 5 and 8-9, electrode system (10) of the present example further includes removable sensors (200). Removable sensors (200) of this example each comprise an insulating upper portion (202), an electrolytic hydrogel lower portion (204), and a conductive center portion (206) positioned between upper and lower portions (202, 204). Conductive center portion (206) comprises a plurality of outwardly extending conductive tabs 208. Each sensor (200) is configured to be inserted in the central opening (106) of a corresponding electrode module (100) and fit snugly therein. In some settings, each electrode module (100) in an electrode system (10) has an associated removable sensor (200) inserted therein; though some electrode modules (100) may lack an associated electrode module (100) in some settings. Inclined surface (108) of upper clamshell member (102) at the perimeter of opening (106) may facilitate insertion of sensor (200) in opening (106), such as by guiding sensor (200) into opening. Of course, as with other features described herein, inclined surface (108) is merely optional, and may be modified, substituted, supplemented, or omitted as desired.

When removable sensor (200) is inserted in electrode module (100), and the corresponding head frame (24) is secured to a test subject's head, removable sensor (200) is configured such that electrolytic hydrogel lower portion (204) contacts the scalp of the test subject. For instance, sensor (200) may have a height such that hydrogel lower portion (204) protrudes below lower flange (174) of snap adapter (170) while insulating upper portion (202) is vertically positioned at or near inclined surface (108) of upper clamshell member (102). Alternatively, sensors (200) may have any other suitable dimensions. Furthermore, depending on the positioning of a given electrode module (100), the associated electrolytic hydrogel lower portion (204) may contact some other part of the test subject's head or body. For instance, hydrogel lower portion (204) may simply contact the hair on the test subject's head; and electrode system (10) may still work properly even if sensors (200) only contact the hair on the test subject's head without necessarily contacting the skin on the test patient's scalp. Due to the electrolytic properties of the electrolytic hydrogel lower portion (204), electrolytic hydrogel lower portion (204) may pick up voltages or signals (e.g., ERP signals, etc.) from the test subject's (e.g., patient's) skin. Electrolytic hydrogel lower portion (204) may collect data without needing to be pasted or glued to the test subject's head, as the hydrogel itself may sufficiently adhere to the subject's head while also allowing removable sensor (200) to be pulled away from the subject's head with relative ease.

As noted above, tabs (208) of the present example are formed as unitary extensions of a conductive member (206) that is disposed between insulating upper portion (202) and electrolytic hydrogel lower portion (204). Conductive member (206) and tabs (208) are configured such that tabs (208) are resiliently biased to assume radially outwardly extending orientations, as shown in FIGS. 5 and 8-9. It should be understood that when sensor (200) is inserted in opening (106) of electrode module (100), tabs (208) contact conductive ring (150), which is exposed in the inner diameter of opening (106) as shown in FIG. 7. For instance, tabs (208) may resiliently bear against conductive ring (150) when sensor (200) is inserted in opening (106). Such contact between tabs (208) and conductive ring (150) may provide a path for communication from conductive member (206) to conductive ring (150) as described in greater detail below. In addition, elastomeric properties or other properties of insulating upper portion (202) and/or hydrogel lower portion (204) may help retain sensor (200) in opening (106) of electrode module. In addition or in the alternative, sensor (200) may be oversized relative to opening (106), such that sensor (200) is snugly or interferingly fit in opening (106). Other ways in which sensor (200) may be substantially retained in opening (106) will be apparent to those of ordinary skill in the art in view of the teachings herein.

Conductive member (206) and tabs (208) may be formed of silver-silver chloride and/or any other suitable material or materials. Conductive ring (150) may also be formed of silver-silver chloride and/or any other suitable material or materials. With conductive member (206) and tabs (208) being in direct contact with electrolytic hydrogel lower portion (204), it should be understood that voltages or signals that are picked up by electrolytic hydrogel lower portion (204) may be further communicated to and through tabs (208). With tabs (208) being in contact with conductive ring (150) when sensor (100) is inserted in opening (106) of electrode module (100), tabs (208) may thus communicate voltages or signals picked up by electrolytic hydrogel lower portion (204) to conductive ring (150), which may in turn communicate such voltages or signals to sensing circuitry of circuit board (130). An amplifier on circuit board (130) (or elsewhere) may amplify the signal, and other components within the sensing circuitry may perform other processing of the signal if desired, and the signal may then be communicated away from electrode module (100) via flexible circuitry in one or more flexible connectors (50). The signals may thus ultimately be communicated to control box interface module (30) via flexible connectors (50) and then on to control box (40) via cable (42).

In some versions, removable sensors (200) comprise HydroDot® Disposable EEG Electrodes or HydroDot® Biosensors by HydroDot, Inc. of Westford, Mass. Various aspects of the HydroDot® Disposable EEG Electrode Application System are discussed in U.S. Pat. No. 5,479,934, entitled "EEG Headpiece with Disposable Electrodes and Apparatus and System and Method for Use Therewith," issued Jan. 2, 1996, which is incorporated by reference herein. Of course, various components of electrode system (10), including but not limited to removable sensors (200), may be configured, modified, and/or operable in accordance with any suitable teachings in U.S. Pat. No. 5,479,934. Indeed, various ways in which the teachings herein may be combined with the teachings of U.S. Pat. No. 5,479,934 will be apparent to those of ordinary skill in the art. It should also be understood that removable sensors (200) are not necessarily required in all versions. For instance, electrode modules (100) may be configured such that they have an electrical interface with the test subject's head and/or some other type of interface with the test subject's head and/or other body part through an injectable gel or in any other suitable fashion.

While sensors (200) of the present example have a substantially cylindraceous shape, it should be understood that sensors (200) may alternatively have any other shape. By way of example only, sensors (200) may have a cubical shape, a right cuboidal shape, a conical shape, a frustoconical shape, a pyramidal shape, a spherical shape, and/or any other suitable shape. Similarly, while conductive rings (150) of the present example have a substantially circular shape, it should be understood that conductive rings (150) may alternatively have any other shape. By way of example only, conductive rings (150) may have a square shape, a rectangular shape, a triangular shape, and/or any other suitable shape. Still other suitable configurations of and relationships between sensors (200) and conductive rings (150) will be apparent to those of ordinary skill in the art in view of the teachings herein.

In the present example, electrode system (10) comprises eight electrode modules (100). As another merely illustrative example, electrode system (10) may comprise twenty three electrode modules (100). Of course, electrode system (10) may alternatively comprise any other suitable number of electrode modules (100). It should also be understood that electrode modules (100) may be arranged in a variety of ways. By way of example only, various suitable arrangements are disclosed in the documents that are cited herein.

Signals obtained using electrode system (10) may be processed in accordance with the teachings of U.S. Pub. No. 2008/0208072, entitled "Biopotential Waveform Data Fusion Analysis and Classification Method," published Aug. 28, 2008, the disclosure of which is incorporated by reference herein and appended hereto. Alternatively, signals obtained using electrode system (10) may be processed in any other suitable fashion. In addition, various suitable ways in which electrode system (10) may be used (including but not limited to signal processing) are disclosed in the various documents cited herein. Still other suitable ways in which electrode system (10) may be used will be apparent to those of ordinary skill in the art in view of the teachings herein. It is contemplated that the teachings herein may be incorporated into or otherwise combined with the systems, components, and methods disclosed in the documents cited herein, in numerous ways. Suitable ways in which the teachings herein may be incorporated into or otherwise combined with the teachings of the documents cited herein will be apparent to those of ordinary skill in the art in view of the teachings herein.

Other features of the present electrodes and system will be understood by those of ordinary skill in the art in view of the teachings herein and in the materials appended hereto. Furthermore, various modifications, substitutions, supplementations, etc. will be apparent to those of ordinary skill in the art in view of the teachings herein and in the materials appended hereto. Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of claims that may be presented, and is understood not to be limited to the details of structure and operation shown and described in the specification and drawings.

I claim:

1. An electrode system, comprising:
  (a) a plurality of electrode modules, wherein each electrode module of the plurality of electrode modules defines a substantially central opening, wherein each electrode module further comprises a conductive ring, wherein each conductive ring is substantially coaxial with the substantially central opening of the associated electrode module;
  (b) a plurality of flexible connectors coupled with the plurality of electrode modules, wherein the flexible connectors comprise flexible circuitry configured to communicate signals from the electrode modules, wherein the flexible circuitry comprises traces formed on a flexible substrate; and
  (c) a plurality of sensors, wherein each sensor of the plurality of sensors is configured to removably couple with a corresponding one of the plurality of electrode modules, wherein the plurality of electrode modules are configured to sense evoked response potentials from a test subject, wherein each sensor is further configured to communicate sensed evoked response potentials to the associated electrode module, wherein each sensor comprises at least one outwardly extending conductive tab, wherein the outwardly extending conductive tab is configured to contact the conductive ring of the associated electrode module.

2. The electrode system of claim 1, wherein each sensor is positioned within the substantially central opening of the associated electrode module.

3. The electrode system of claim 1, wherein each electrode module further comprises a housing defining the substantially central opening, wherein the conductive ring of each electrode module is at least partially exposed in an inner diameter of the substantially central opening defined by the housing of the associated electrode module.

4. The electrode system of claim 1, wherein each of the electrode modules comprises an upper clamshell member, a lower clamshell member, and a circuit board, wherein the circuit board is positioned between the upper clamshell member and the lower clamshell member, wherein the upper clamshell member and the lower clamshell member are coupled together.

5. The electrode system of claim 4, wherein the circuit board of each electrode module further comprises a socket, wherein part of each flexible connector is inserted in the socket of a corresponding one of the electrode modules to provide communication between the circuit board of each electrode module and the flexible circuitry of a corresponding one of the flexible connectors.

6. The electrode system of claim 1, wherein each electrode module comprises a corresponding amplifier.

7. The electrode system of claim 1, further comprising a head frame configured to fit on the head of a test subject, wherein the electrode modules are removably coupled with the head frame.

8. The electrode system of claim 7, wherein the electrode modules are coupled with the head frame by snap fittings.

9. The electrode system of claim 7, wherein the head frame comprises a plurality of elastic members.

10. The electrode system of claim 1, further comprising a control box in communication with the electrode modules.

11. The electrode system of claim 10, wherein the control box comprises a storage medium storing evoked response testing protocols and a processor operable to execute evoked response testing via the electrode modules in accordance with the stored evoked response testing protocols.

12. The electrode system of claim 11, wherein the storage medium of the control box is further operable to store results of the evoked response testing.

13. The electrode system of claim 10, further comprising a control box interface module positioned between the control box and the electrode modules, wherein the control box interface module provides an interface between the control box and the electrode modules.

14. The electrode system of claim 13, wherein the electrode modules are in communication with the control box interface module via one or more of the flexible connectors, wherein the control box is in communication with the control box interface module via one or more cables.

15. The electrode system of claim 1, wherein each sensor of the plurality of sensors further comprises an insulating upper portion and an electrolytic hydrogel lower portion.

16. An electrode system, comprising:
  (a) a plurality of electrode modules, wherein each of the electrode modules comprises circuitry, wherein the circuitry of each electrode module comprises an amplifier;
  (b) a plurality of flexible connectors coupled with the plurality of electrode modules, wherein the flexible connectors comprise flexible circuitry configured to communicate signals from the electrode modules; and
  (c) a plurality of sensors, wherein each sensor of the plurality of sensors is configured to removably couple with a corresponding one of the plurality of electrode modules, wherein the plurality of electrode modules are configured to sense evoked response potentials from a test subject, wherein each sensor is further configured to communicate sensed evoked response potentials to the associated electrode module, wherein the amplifier of each electrode module is configured to amplify the sensed evoked response potentials communicated to the associated electrode module, wherein each sensor of the plurality of sensors comprises an upper portion, a lower portion, and a conductive portion between the upper and lower portions, wherein the conductive portion comprises at least one conductive tab extending outwardly relative to the upper portion and the lower portion.

* * * * *